United States Patent [19]
Benton et al.

[11] Patent Number: 5,962,249
[45] Date of Patent: Oct. 5, 1999

[54] SIZED-BASED MARKER IDENTIFICATION TECHNOLOGY

[75] Inventors: Bret Benton, Burlingame; Keith Bostian; Molly B. Schmid, both of Menlo Park; Dongxu Sun, Cupertino; Jerry M. Buysse, Los Altos, all of Calif.

[73] Assignee: Microcide Pharmaceuticals, Inc., Mountain View, Calif.

[21] Appl. No.: 08/770,246

[22] Filed: Dec. 20, 1996

Related U.S. Application Data

[60] Provisional application No. 60/009,067, Dec. 22, 1995.
[51] Int. Cl.$^6$ .............................. C12Q 1/02; C12Q 1/68; C12N 15/09; C12N 15/90
[52] U.S. Cl. .............................. 435/29; 435/6; 435/172.3; 435/235.1; 435/252.3; 435/254.11; 435/325; 435/419
[58] Field of Search .................................. 435/6, 30, 29, 435/91.2, 172.1, 172.3, 325, 410, 419, 252.3, 254.11, 320.1, 883, 235.1; 536/23.1, 24.2; 935/66, 67, 68, 70, 72

[56] References Cited

FOREIGN PATENT DOCUMENTS 9640979 12/1996 WIPO .

OTHER PUBLICATIONS

Mahan et al. "Selection of bacterial virulence genes that are specfically induced in host tissues" *Science* 259: 686–688, Jan. 1993.

Hensel et al., "Simultaneous Identification of Bacterial Virulence Genes by Negative Selection," *Science* 269:400–403 (1995).

Horinouchi and Weisblum, "Nucleotide Sequence and Functional Map of pE194, a Plasmid that Specifies Inducible Resistance to Macrolide, Lincosamide, and Streptogramin Type B Antibiotics," *J. Bacteriology* 150:904–814 (1982).

Lee et al., "Construction of single–copy integration vectors for Staphylococcus aureus," *Gene* 103:101–105 (1991).

Pike et al., "Development and design of a novel in vivo chamber implant for the analysis of microbial virulence and assessment of antimicrobial therapy," *Microbial Pathogenesis* 10:443–450 (1991).

Rosey et al., "Dual flaA1 flaB1 Mutant of Serpulina hyodysenteriae Expressing Periplasmic Flagella Is Severely Attenuated in a Murine Model of Swine Dysentery," *Infection and Immunity* 64:4154–4162 (1996).

*Primary Examiner*—George C. Elliott
*Assistant Examiner*—Thomas G. Larson
*Attorney, Agent, or Firm*—Lyon & Lyon LLP

[57] ABSTRACT

A method for identifying a cell or strain of cells containing a mutation in a gene involved in growth, comprising the steps of forming a labeled set of strains comprising a plurality of members, each member of the set containing an exogenous DNA fragment of a defined length stably integrated into the chromosome of a member, the defined length in each member differing from the defined length in other members, subjecting the labeled set of strains to mutagenesis so as to obtain mutants from each member of the set of strains, and introducing the mutant strains into a growth environment for a period of time sufficient for growth of a non-mutated strain and determining which strains have reduced growth compared to a non-mutated strain, by determining the presence and size of exogenous DNA fragments relative to each other using PCR and agarose/polyacrylamide gel electrophoresis.

34 Claims, 7 Drawing Sheets

PLASMID CONSTRUCTION FOR S. aureus SMIT
II. PROVIDE L54a INTEGRASE IN TRANS

SIZED-BASED MARKER IDENTIFICATION TECHNOLOGY

RELATED APPLICATION

This application claims priority to Benton et al., U.S. Provisional Application No. 60/009,067, filed Dec. 22, 1995, which is hereby incorporated by reference in its entirety, including drawings.

BACKGROUND OF THE INVENTION

This invention relates to methods and reagents for marking strains of microorganisms and cells and for the identification of genes.

The following is a general discussion of the relevant art, none of which is admitted to be prior art to the invention.

Bacterial infections of host organisms create difficulties in a variety of different fields, notably in human medicine. In order to develop effective treatments to control such bacterial infections, it is frequently important to understand the mechanisms involved in the pathogenesis process. Therefore, it is useful to identify and isolate the genes involved in pathogenesis, which can also be used as targets in various methods for the identification and development of anti-bacterial drugs.

Several different approaches and methods have been used to identify bacterial genes involved in pathogenesis. The various approaches seek to identify pathogenesis-related genes, based on one or more characteristics linking the expression of the gene with the pathogenesis process. Thus, various approaches seek to identify sets of genes, such as genes encoding various toxins and protein factors involved in binding to and invading host cells, genes that are preferentially expressed in vivo (e.g., by differential display, differential hybridization, or by use of "In vivo Expression Technology", IVET), and genes that are required for in vivo survival and growth. While the methods previously used for these approaches have been able to identify some pathogenesis related genes, those methods have limitations as described below:

1. By isolating genes encoding toxins and other known virulence factors, the regulation of these genes and their roles in the pathogenesis process can be studied in more detail. Identification of genes encoding exotoxins and other readily-recognized genes requires substantial effort in investigation of the gene products and in establishing their role in pathogenesis. In addition, many genes involved in pathogenesis are not exotoxins, nor are they readily recognized as virulence factors. Thus, many genes which are specifically expressed in vivo and/or are essential for in vivo survival or growth cannot be identified by this approach.

2. Differential display examines mRNAs that are specifically present after in vivo growth or after growth under conditions that mimic the in vivo environment. This method requires that a particular in vivo specific mRNA be present at a relatively high level to be detected, which may not always occur. In addition, the presence of large amounts of rRNA and other RNAs can often reduce the power of this technique.

3. The IVET technology likewise identifies genes which are preferentially expressed in vivo, and has been used to identify many such genes (Mahan et al., 1993, *Science* 259:686–688). However, most of the genes isolated by this method are merely housekeeping genes and thus are not useful as targets for anti-bacterial therapy. Furthermore, since IVET identifies the in vivo expressed genes by the ability of their promoter to direct expression of a selectable gene involved in specific nutrient synthesis or antibiotic resistance, the promoters must be strong enough to be identified. Consequently, in vivo expressed genes with weak promoters will fail to be identified in this method. Finally, IVET technology does not provide mutants useful in establishing a direct role in pathogenesis for the in vivo expressed gene.

4. To isolate genes that are essential for in vivo survival/ growth, a method of using transposons to tag and mutagenize cells was developed (Hensel et al., 1995, *Science* 269:400–403). In this method, a mixed population of such mutagenized cells is grown and the mutants that fail to survive and grow in vivo are detected by the disappearance of the corresponding specific oligonucleotide tag. The corresponding gene is then identified as it is the transposon-interrupted gene for that mutant strain. While new in vivo essential genes have been identified in *Salmonella typhimurium* using this method, several factors limit its use in a range of bacteria under different conditions.

First, as transposons are used as the tool for self-tagging and mutagenesis, the method cannot be used in bacteria which do not possess a random insertion transposon system. This prevents the use of this method in many medically important bacteria or in other pathogens such as fungi and viruses.

Second, even in organisms with developed random transposon technology, the only type of mutants generated by this method are transposon-insertional mutants. This excludes, or at least severely limits, the use of other mutagens to generate other types of mutants.

Third, the use of relatively large amounts of radioactive material in producing labeled probes, and the laborious procedures of DNA hybridization and detection make this method difficult, slow, expensive, and environmentally unfavorable.

Fourth, the presence, in some organisms, of "hot spots" for transposon insertion (a relatively common phenomenon) and cross-reactivity among oligonucleotide tags can reduce the effectiveness of the screen and create interpretive difficulties.

SUMMARY OF THE INVENTION

Applicant has developed a new technology which is useful for identifying particular genes in a broad range of organisms, such as bacteria, viruses, fungi, other lower eukaryotes, and animal and plant subcultures.

This technology generally involves marking cells through the use of different sizes of exogenous DNA fragments and identifying strains of those marked cells by examining the loss or relative frequency change of specific marker fragments in a particular population of marked cells. The methods can be used, for example, to identify mutant cells or to understand the population dynamics of the marked cell strains in an environment. In this size-based marker identification technology (SMIT), a basic set of isogenic strains or cell lines (hereinafter "strains" refers to both strains and cell lines unless otherwise indicated) is constructed; each strain has a different exogenous DNA fragment, preferably inserted at the same location on the chromosome in each strain. The DNA fragments in different strains differ in length, and are flanked by a common pair (or one of a few common pairs) of oligonucleotides that can be used as polymerase chain reaction (PCR) primers. The length differences in strains of cells sharing the same flanking primers are so constructed that, upon amplification of pooled chromosomal DNA from these strains by PCR, each of the fragments can be clearly seen and distinguished on a standard agarose or polyacrylamide gel. The presence of a particular length band identifies the specific strain which contains that exogenous DNA fragment.

Once this set of basic parental strains is constructed, it can be mutagenized to allow identification of genes, e.g., genes important for in vivo growth from pathogenic bacteria. Specifically, each of the marked strains can be separately mutagenized by any of a large number of mutagenesis techniques, e.g., transposon insertion or chemical or physical mutagenesis. Mutant cells from these mutagenized strains are pooled and used to infect a host, e.g., an animal host. Mutant cells are recovered at specified times after infection; DNA is extracted from the cells and is subjected to PCR. If a mutant grows poorly or not at all, its corresponding PCR band will be missing or under-represented, indicating that the cells of the mutant strain contain an altered gene that is important for in vivo growth.

SMIT is particularly suited for the identification of bacterial genes that are important for in vivo growth and pathogenesis in an animal or plant host, or for the establishment of biofilm growth on an inert matrix but is also useful for the identification of particular genes in strains of other pathogens, such as viruses and fungi. As with bacterial genes, viral or fungal genes that are important for in vivo growth can also be identified using molecular biology techniques appropriate for the particular organism. Once a strain containing a mutation in a gene important for in vivo growth is identified, this gene can be cloned utilizing techniques familiar to those who practice the art.

SMIT is also useful for the identification of strains for a variety of organisms, including non-pathogenic bacteria, viruses, fungi or cultured cells from plants and animals. Thus, in general, SMIT allows the identification of particular genes which are essential or important for growth in a particular environment. However, SMIT can also be utilized in a variety of other types of test studies. These studies would include tracking populations of organisms or cells. For example, the distribution of a microbial population in an ecosystem can be studied by marking the cells using SMIT, mutagenizing them if required, and releasing them back into the particular environment. A further application involves marking the cells using SMIT and following the fate of the organisms in an infected host as the organisms disperse to various tissues post-infection. Similarly, migration and transmission behaviors of microbes (e.g., microbial pathogens) and agriculturally important insect pests can be monitored by labeling different strains of the pest using SMIT, and determining the presence/absence of the specific strains at various locations and times. For example, the transmission of bacteria between different members of a population of animals can be monitored by infecting particular individuals in that population with labeled *E. coli* and determining the presence or absence of labeled bacteria in stool samples. Likewise, plant cells can be marked using SMIT to allow population geneticists to track the growth of particular strains or species of plants. Also, certain stem cells can be marked in vitro and then reintroduced into an organism to study the development and distribution of those and progeny cells.

Thus, in a first aspect the present invention features a method for identifying a strain of cells containing a mutation in a gene involved in in vivo survival and growth. The method comprises the steps of: 1) Forming a labeled set of strains comprising a plurality of members. Each member of the set contains an exogenous DNA fragment of a defined length stably integrated into the chromosome of that member. The defined length of the exogenous DNA fragment in each member differs from the defined length of the DNA fragment in other members; 2) The labeled set of strains is subjected to mutagenesis so as to obtain mutants from each member of the set of strains; 3) Cells of mutant strains are introduced into a growth environment for a period of time sufficient for growth of non-mutated strains and mutants whose growth is not impaired; 4) Strains having a mutation in a gene involved in in vivo survival and growth have altered growth compared to non-mutated strains. Such mutated strains are identified by determining the presence or absence of the marked strains of the set by determining the size and amount of the exogenous DNA fragments relative to each other.

A "strain" or "strain of cells" is meant to include any microorganism or cell line, such as bacteria, viruses, fungi, plant cells, and animal cells. The term refers to a subset of a species. Different strains of a species have identifiable genetic differences, e.g., the presence of different size marker sequences. The term can refer to one or more cells, but in general refers to a cell or cells having particular genetic characteristics.

By "mutation" is meant any alteration in genetic material, i.e., a change in sequence of a nucleic acid having coding sequences.

By "essential" is meant necessary for the growth of a cell or strain in a particular environment. For a bacterial strain, growth would be in an environment either inside or outside a host organism. Essential does not necessarily mean required for growth in culture. For animal or plant cells, "essential" refers to growth in cell culture or in an organism.

By "growth" is meant an increase or decrease in cell number.

By "plurality" is meant more than one member. A plurality would typically consist of a number of labeled strains or cells that would be useful for the identification of particular genes. For example, in a bacterial strain such as *Staphylococcus aureus* this could be a set of 96 labeled strains. The number of labeled strains which would preferably comprise a plurality primarily depend upon the size of the genome of the particular organism, the numbers of target genes to be mutagenized, the methods used for mutagenesis, and the capacity to screen mutants. The larger the genome of the organism, the greater the number of mutants that should preferably be screened. Those of ordinary skill in the art are familiar with techniques to determine the number of mutants that need to be screened to identify an essential gene based on the size of the genome.

By "exogenous DNA fragment" is meant that the fragment is obtained from a source that is different from the cell into which it is inserted.

By "defined length" is meant that the exogenous DNA fragment comprises a known or estimated number of nucleotides which allows it to be distinguished from other fragments, such as on an agarose or polyacrylamide gel.

By "stably integrated" is meant that the exogenous DNA fragment is inserted into a chromosome of a cell so that when the cell replicates the fragment is passed onto to daughter cells along with other genetic material.

By "mutagenesis" is meant any method that structurally alters genetic material, including point mutations, insertions, and deletions.

By "growth environment" is meant to include in an organism, outside an organism in a natural environment such as an ecosystem, or in cell culture. An organism may include an animal or plant host.

By "altered growth" is meant either an increase or decrease in growth.

By "determining the presence or size" is meant any method familiar to those who practice the art for identifying and determining or estimating sizes of DNA fragments. Such size determination methods include electrophoresis on agarose or polyacrylamide gels, and identification methods include direct staining with dyes such as ethidium bromide, and Southern hybridization with specific probes.

In preferred embodiments of the invention the strains of cells are bacteria, viruses, fungi, plant cells, or animal cells.

In further preferred embodiments, mutagenesis involves the use of transposons or other insertional mutagens such as insertional plasmids; mutagenesis involves chemical mutagens; mutagenesis occurs spontaneously; mutagenesis comprises the use of ultraviolet light; mutagenesis is by in vitro means, such as site-directed mutagenesis and incorporation of mismatched nucleotides during DNA synthesis by PCR or by chemical synthesis under specially designed conditions. Also, independently in preferred embodiments, the bacteria is of the species Staphylococcus aureus; the growth environment is in an animal host; and integration of the exogenous DNA fragment is at the same chromosomal location in all members of the plurality.

By "transposon" is meant any DNA sequence that can move from one chromosomal location to another or from a delivery plasmid to a chromosomal location, with or without inverted repeat sequences.

By "insertional mutagen" is meant any element able to cause an alteration of a gene by inserting nucleotide sequences into a gene. Such mutagens include suicide integration plasmids in bacteria and fungi, viruses and nucleotide sequences transferred by transfection or microinjection.

By "chemical mutagenesis" is meant alteration of nucleotide sequence by the use of chemical such as diethyl sulfate (DES), ethyl methane sulfate (EMS), nitrosoguanadine, hydroxylamine, and aminopurine.

By "spontaneous mutagenesis" is meant naturally arising mutations.

By "mutagenesis comprising the use of ultraviolet light" is meant use of radiation around 254 nm that is absorbed by DNA so as to cause alterations in DNA structure such as thymine dimers, which may result in hereditary changes. Other physical methods include the use of other radiation, such as γ-ray radiation.

By "in vitro mutagenesis: is meant the generation of alterations in DNA sequence outside a cellular environment, such as site-directed mutagenesis using synthetic oligonucleotides with defined sequences, and incorporation of mismatched nucleotides during DNA synthesis by error-prone PCR or by chemical synthesis under specially designed conditions. The altered DNA sequences are then introduced into the cells by appropriate methods such as transformation, transfection, or micro-injection.

In another embodiment the method further comprises the identification of the gene involved in growth contained in the mutant cell or strain having reduced growth compared to a non-mutated cell or strain in the growth environment.

By "identification of the gene" is meant cloning of a wild type copy of the gene. Methods of cloning particular genes include: isolating plasmid clones of a genomic or cDNA library which complement the growth defect caused by the mutation; using the mutagenizing transposon (if it is the mutagen) as a probe to screen a genomic library; using the transposon as a plasmid vector (if it carries a replication origin functional in another host such as *E. coli*) to clone the gene by digesting and recircularizing the chromosomal DNA; or by other methods that are familiar to those who practice the art.

In a second aspect the invention features a method for producing a plurality of labeled strains which can be individually identified. The method comprises the steps of introducing into a plurality of separate cells an exogenous DNA fragment which differs in length in each separate cell, and is able to stably insert into a chromosome of each separate cell. In general, the individual labeled cells are grown to provide separately identifiable strains of cells; the individual identification is based on joint identification of a large number of cells of a particular strain.

By "individually identified" is meant that cells of a strain can be distinguished from other labeled cells or strains of cells by the particular length exogenous DNA fragment contained in the cell or strain of cells.

In preferred embodiments the cells are bacteria, viruses, fungi, plant cells or animal cells. Independently in further preferred embodiments the bacteria are of the species *Staphylococcus aureus*; and integration of the exogenous DNA fragment is at the same chromosomal location in all members of the plurality.

In a third aspect the invention features a set of labeled cells wherein a chromosome of each cell of the set contains an exogenous DNA fragment which differs in length between each member of the set.

Independently in preferred embodiments the cells are bacteria, specifically including bacteria of the species *Staphylococcus aureus*; the cells are viruses; the cells are fungi; the cells are plants cells; and the cells are animals cells.

In a fourth aspects the invention features a method for monitoring the distribution or fate of a cell in a growth environment. The method comprises the steps of forming a labeled cell with an exogenous DNA fragment of a defined length, stably integrated into the chromosome of the cell, introducing the labeled cell into the growth environment for a period of time sufficient for growth of the cell and determining the distribution or fate of the cell by the presence of the exogenous DNA fragment. The period of time should also be sufficient for mixing, spreading, and/or migration of the progeny cells as appropriate.

As an example of the application of this embodiment, the spreading of an antibiotic-resistant bacterial strain (or a number of such strains) among animal hosts can be investigated by mixing the labeled bacterial cells and injecting them into one or more host animals at appropriate doses. After a suitable period of time (or at various time points), the presence of these strains in the injected animals as well as in the non-injected animals in the same environment can be determined by the presence of bacteria having the specific DNA fragments in properly collected samples (such as from stool, blood, or spleen). The methods of labeling cells and examining the presence of exogenous bands has been described above and is described in greater detail in the detailed description below.

In different uses, the number of cells, of a particular strain to be monitored, which are introduced into a growth environment can vary. For example, for monitoring the fate of a particular stem cell it may be desirable to introduce a single cell. In contrast, for monitoring the distribution of a strain of bacterial cells in an environment (as described above), a large number of cells would typically be introduced.

By "distribution" is meant the location of a cell or the cells of a strain in a host organism or in a natural environment, e.g., an ecosystem.

By "fate" is meant the absence or presence of a cell, the increase or decrease of cell numbers, or alterations of the cellular status, such as those that are the result of differentiation.

The SMIT method offers several advantages over other methods for marking cells or strains and gene identification. Advantages include, but are not limited to the following.

First, SMIT can be utilized with any means of mutagenesis, even spontaneous mutations. This is especially useful for two reasons:

a. Not all mutagenesis methods can be efficiently applied to every type organism. For example, random and efficient transposon mutagenesis systems have not been observed or developed in many bacteria. It is difficult to apply site directed mutagenesis in bacterial strains where the genetics and molecular biology has not been developed. Different chemical and physical (e.g., UV) mutagens may have different killing and mutagenizing effects on different organisms depending on their cell wall and cell membrane structures, DNA compositions, DNA repair systems, etc. Certain mutagens and/or mutagenizing methods may be more suitable than others for a given organism. Therefore, having available a large array of mutagenesis methods to choose from broadens the application of this invention in various organisms.

b. Different kinds of mutations can be generated by using different mutagenesis methods. These include point mutations (such as missense and nonsense mutations and those in the regulatory regions), insertions, and deletions. The mutagenesis methods can be targeted to certain gene(s) or even to certain nucleotides, such as in vitro site-directed mutagenesis, mutagenesis by error-prone PCR and DNA chemical synthesis, and knockout mutants generated by integration and other homologous recombination events. Other mutagenesis methods are rather random, targeting the whole genome, such as many transposons and most chemical and physical mutagens. It has been known that even for mutagens that induce random mutations, their modes of action are quite different from each other, thus generating different types of mutations. Mutations in certain gene(s) having detectable phenotypes may be obtained by one mutagen but not by others. The more mutagenesis methods available, the more likely that a desired mutant form(s) of a gene can be generated. Therefore, it will be especially advantageous if one has the ability to choose different mutagenesis means to mutagenize and identify a large number of genes whose mutant forms share a common phenotype. For example, in searching for genes essential for in vivo growth by transposon mutagenesis, if one such gene is upstream of an in vitro essential gene in the same operon, a transposon insertion in the in vivo gene will greatly diminish or completely block the expression of its downstream in vitro essential gene. This will make it difficult to obtain mutants in the in vivo gene by transposon insertion because mutants are not able to be propagated in vitro due to the polar effect. On the other hand, it is possible to obtain point mutations, such as missense mutations, in the in vivo essential gene without the polar effect, by other means of mutagenesis, e.g., chemical mutagens or UV irradiation.

Second, the SMIT method is not limited to the identification of in vivo essential genes of bacteria or even of other microbes. It can be used to track the behavior, distribution and fate of certain cells in a mixed culture or in an ecosystem. The SMIT method can thus be extended to viruses, fungi and other microorganisms. It can also be extended to cell culture studies of higher animals and plants and used to determine the distribution or fate of eukaryotic cells in an organism.

Third, SMIT utilizes PCR and agarose gels instead of radioactive labels to visualize the presence of markers. Avoidance of the use of radioactive material makes the SMIT method easier, less costly, safer, faster (results available in hours not days), less trouble and more efficient than previously existing methods.

Fourth, SMIT utilizes a set of parental marked cells or strains. Since each marked strain can be mutagenized separately and only one mutant from each mutagenized strain is used in a pool, the chance of having siblings in the same pool will be greatly reduced. Therefore, the population of mutants examined will be more random and more independent. This means higher efficiency than other mutagenesis schemes.

Fifth, the construction of the parental isogenic marked cell sets will, over the long term, save time and effort. The same set of insertion fragments and their flanking primers can be repeatedly used with different mutagenesis procedures and in different growth environments and in different organisms.

Sixth, characterization of the size-markers in the input pools can be carried out in detail, so that when the relative ratios of different marked cells or strains are changed, the results are predictable. In contrast, in other methods, such as those based on transposon-delivered tagging and DNA hybridization, markers in every pool are different from other pools, and the identity of markers in a particular pool of mutants is not predictable. Also, there is always a possibility that the markers in a given pool may cross-hybridize each other, so that some mutants affected in in vivo growth may not be identified.

Other features and advantages of the invention will be apparent from the following description of the preferred embodiments thereof, and from the claims.

BRIEF DESCRIPTION OF THE DRAWINGS

The drawings will first be described.

FIG. 1 is a schematic drawing of an insertion plasmid vector, pMP190, used to introduce exogenous DNA fragments into the chromosome of *Staphylococcus aureus*. The precursor of this plasmid is pMP16, which was constructed by cloning ClaI-linearized pE194 (a natural plasmid, ref. see S. Horinouchi and B. Weisblum, J. Bacteriol. 150:804–814, 1982) into NarI cut pUC19. The pMP16 (6.41 kb) can replicate in both *E. coli* and *S. aureus*. Into EcoR1-BspE1 cut pMP16 (ends filled) was cloned a 280 bp BamH1-HincII fragment (ends filled) from plasmid pBR322. To construct the integration plasmids, the replication origin of pE194 on pMP16 was removed by digesting with EcoR1 and BspE1, filling the cohesive ends with *E. coli* DNA polymerase I Klenow fragment and dNTPs, and then religation. The resulting plasmid has a Sma1 site in the polylinker region of the pUC19 portion, an SgrA1 site, and contains the ermC gene for erythromycin-resistance selection. Since the pE194 replication origin is removed, the plasmid cannot replicate in *S. aureus* cells. However, when a *S. aureus* chromosomal fragment is cloned into the plasmid, the plasmid can integrate into the chromosome via homologous recombination. By transforming the insert-containing plasmid into *S. aureus* cells and selecting for erythromycin resistant colonies, cells with integrated plasmid can be isolated. To introduce still an additional rare site (AscI), the plasmid was digested with NarI, which has three sites, all located in the 280 bp region originally from pBR322. Due to the site preference of NarI enzyme, only one of the three sites is cut completely under our normal digestion conditions. The NarI enzyme recognizes and cuts at sequence GGCGCC, producing a 5' overhang of CG. The ends of NarI digested plasmid were filled to form blunt ends and then religated. The end-filling and religation steps changed the NarI site GGCGCC into GGCGCGCC, which is the site for another rare cutter, AscI. The resulting plasmid possesses three rare sites—SmaI, SgrAI and AscI.

In the plasmid vector described above, the pUC19 derived lacZ gene portion encoding the α-peptide has been destroyed so that the convenient blue-white screen is no longer available. A new vector, pMP190, was constructed by replacing the destroyed lacZ gene portion of pUC19 with a complete, functional one. To do this, plasmid pUC19 was digested with NdeI, the ends were filled, and then digested with AflIII. The resulting 623 bp fragment that contains the entire lacZ gene a-peptide fragment was cloned into the preceding plasmid, which was digested with AflIII and SmaI. Colonies that carried the correct plasmid (pMP190) all turned blue on plates containing x-gal.

In FIG. 4, pMP274 is digested with EcoRI and HindIII to generate a linear molecule capable of ligating to a second fragment carrying the chloramphenicol acteyltransferase gene (cat) from plasmids pER186 and pER194 (Rosey, et al, 1996, Infection and Immunity 64:4154–4162). Ligation of these fragments generates pMP274/CAT. PCR amplification of the 400 bp attP region of phage L54a provides an EcoRI fragment that is ligated upstream of the cat gene, generating two versions of pMP274/CAT/attP, with different orientations of the cat gene in respect to attP. Size marker DNAs are cloned into the unique BamHI site of pMP274/CAT/attP for transformation and integration into the S. aureus attb chromosomal site.

FIG. 5 describes the construction of a plasmid providing L54a integrase function in trans, to support integration of the pMP274/CAT/attP vector. pMP16 was constructed by fusion of pUC19 and pE194. A 1350 bp PCR product encompassing the L54a int gene is cloned into the unique BamHI site of pMP16, generating pMP16/INT. To implement integration of a size-marker into the S. aureus genome, the strain is first transformed with pMP/INT, selecting for erythromycin resistance; subsequently, erythromycin-resistant clones are transformed with a pMP274/CAT/attP vector containing a given size-marker DNA. As the pMP274/CAT/attP vector does not contain a replication origin capable of supporting plasmid replication in the S. aureus host and owing to the presence of attP, the integrase provided by pMP16/INT mediates site-specific integration of pMP274/CAT/attP at the attB locus. This process is used to integrate different sized markers in individual strains of S. aureus.

DESCRIPTION OF THE PREFERRED EMBODIMENTS

The following examples primarily describe the use of SMIT in *Staphylococcus aureus* by the specified methods. However, it should be clear that the invention can be practiced in many ways and using many different cell types; some such methods will present merely minor technical variations of the methods discussed below. In particular, certain examples below utilize particular plasmid constructs, however, those skilled in the art can produce other plasmids suitable for use in SMIT using methods known in the art.

Preferably, a set of 96 basic strains is constructed. The inserts for these strains consist of 24 fragments of different sizes flanked by a common pair of primers. To construct 96 basic strains, 4 pairs of primers are required, each pair of primers are linked to a set of 24 fragments.

Figure 1:
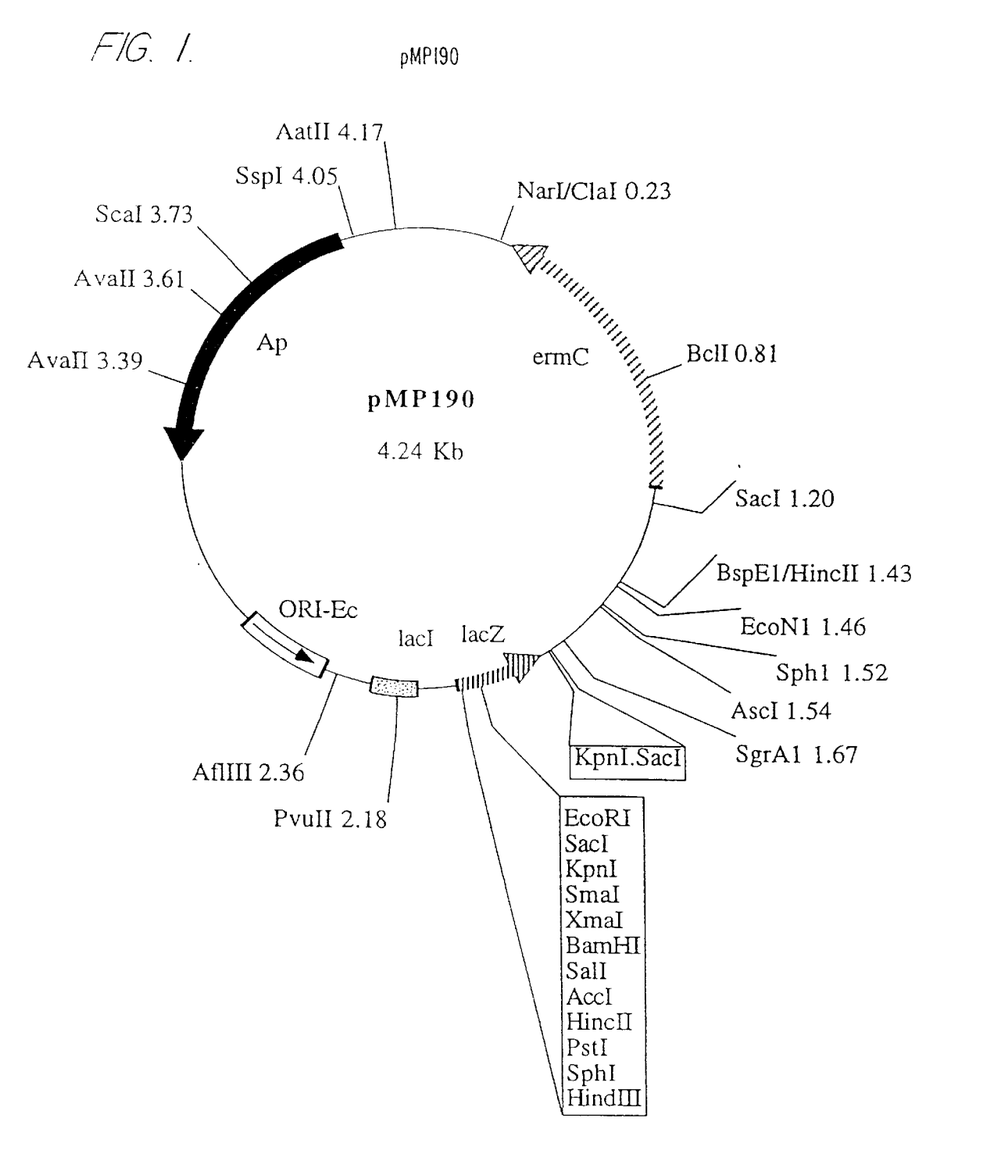

Example 1: Construction of marker fragments library Construction of insertion plasmid vectors The vectors are used to clone exogenous DNA fragments and introduce them into the chromosome of S. aureus. They have the following structural components as illustrated by pMP190 in FIG. 1. The vector plasmids have a replication origin (such as colE1) that is functional in E. coli but not in S. aureus, an antibiotic resistance gene (amp) selectable in E. coli cells, the ermC gene which confers erythromycin resistance in S. aureus, a temperature-sensitive pE194 replication origin (ts-pE194-ori) that functions in S. aureus at permissive temperature (30° C.), and a "cloning-integration cassette" (CIC). The CIC consists of an S. aureus DNA fragment, which is disrupted by the tet gene (conferring tetracycline resistance in S. aureus) and an oligonucleotide sequence of about 40–50 base pairs. The S. aureus DNA fragment is not essential for either in vivo or in vitro growth and is not related to pathogenesis pathways, so disruption by the inserts result in no change in growth and/or pathogenesis properties. This fragment is used to introduce the inserts (including the tet gene and the primer-flanked sized markers) within it into S. aureus chromosome by homologous recombination. The tet gene is used for selection of recombinants that contain the inserts. In the middle of the 40–50 bp oligonucleotide sequence there is a unique restriction site, preferably a SalI site. Upon digestion with the unique restriction enzyme and insertion of exogenous DNA fragments at this site, the split oligonucleotide can be used as a pair of primers (P1 and P2) for PCR. Four such vectors which are different from each other only in the primer regions (P1 and P2) are used.

Figure 2:
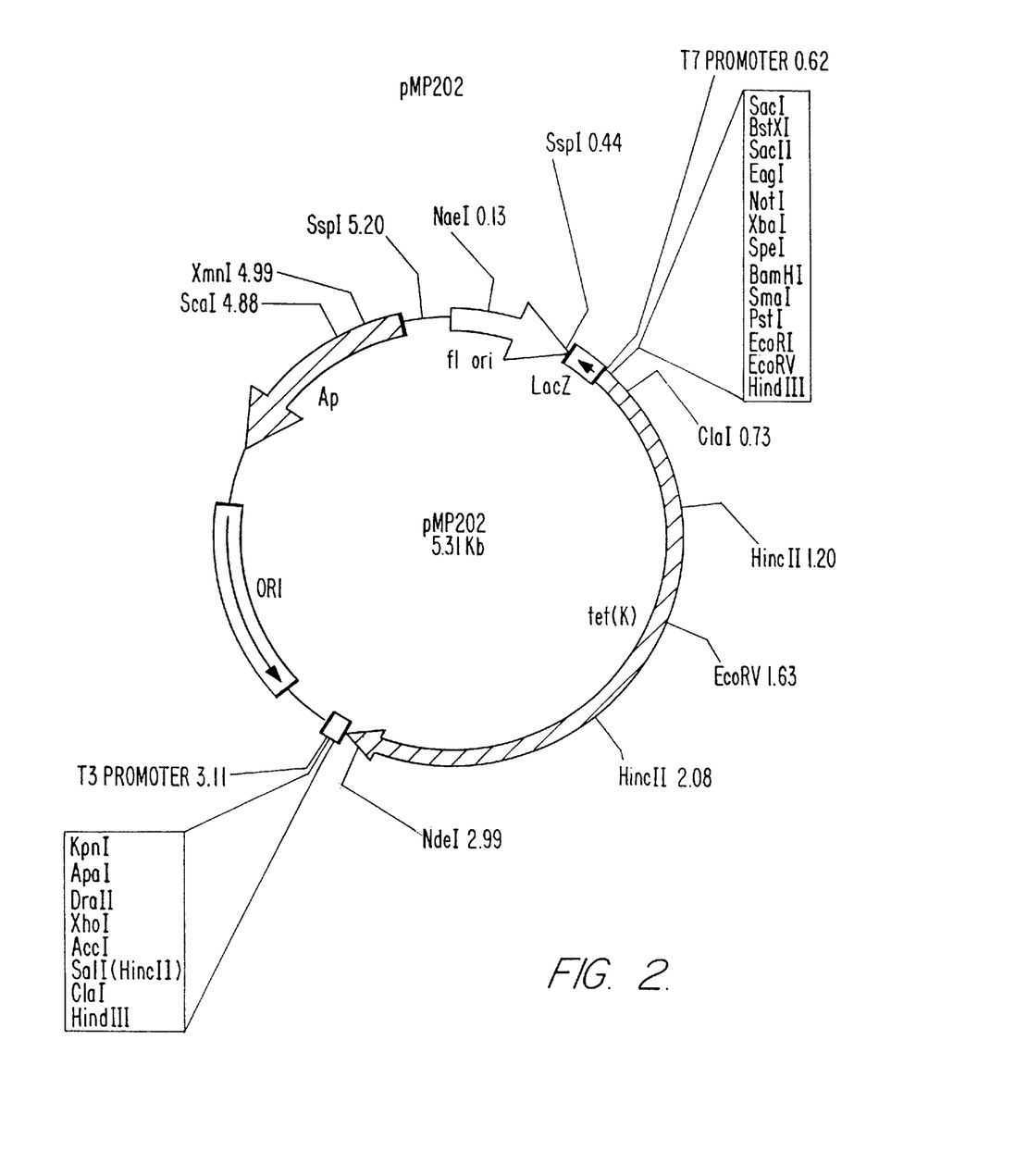
FIG. 2 is a schematic drawing of pMP202, which is a 5.31 kb plasmid consisting of the 2350 bp tet(K)-containing HindIII fragment derived from the naturally occurring plasmid pT181, subcloned into the commercial pBluescript KS+.
Figure 3:
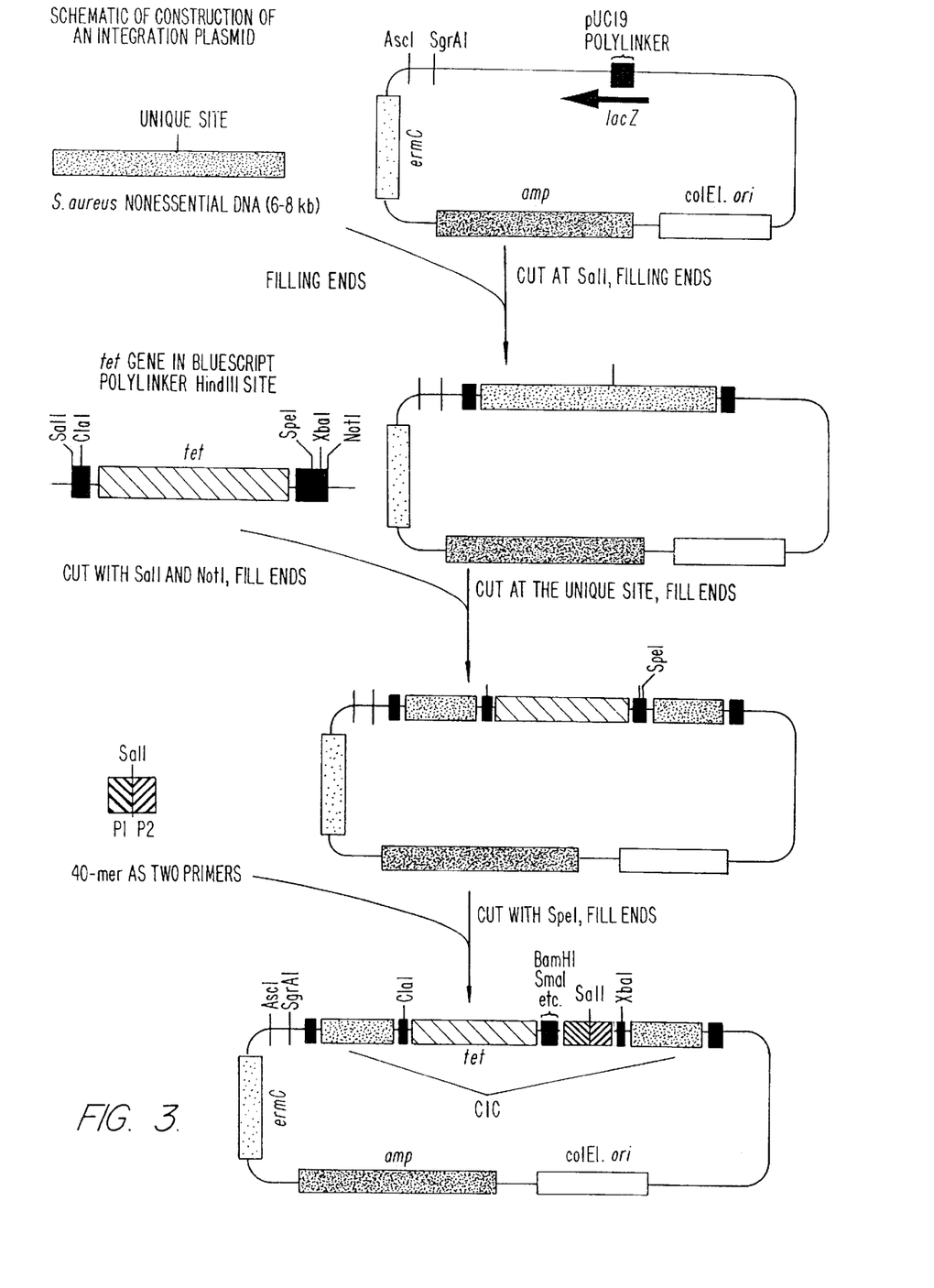
FIG. 3 is a schematic drawing of the construction of an insertion plasmid vector containing a CIC (Chromosomal Integration Cassette).

Construction of this plasmid is illustrated in FIG. 3 and generally described in a–d below:

a. A large DNA fragment of S. aureus (6–8 kb) that is not involved in either cell growth or pathogenesis is selected as the "home" for inserting sized markers. This fragment, which has a unique restriction site approximately in the middle, is cloned into an integration plasmid, e.g., into the SalI site in plasmid pMP190.

b. The ts-pE194-ori is obtained by PCR amplification from plasmid pLTV1. The PCR product is then cloned into the SalI site into the AscI site of the plasmid from step a.

c. The resulting plasmid is cut in the middle of the inserted S. aureus DNA fragment with the unique enzyme. The ends are filled and ligated to an ends-filled 2.4 kb SalI-XbaI fragment from pMP202 (restriction map shown in FIG. 2) that contains the tet gene as well as a number of restriction sites (including SpeI) at both ends.

d. The resulting plasmid is then cut with SpeI, and ligated with each of the 4 different 40–50 bp oligonucleotides which share no homology with S. aureus chromosomal DNA. The oligonucleotides are designed to have a SalI site in the middle. The SalI site will be used for inserting exogenous DNA fragments of varying sizes.

Source of marker fragments

Random DNA fragments from unrelated organisms or chemically synthesized DNA can be used. DNA from other organisms is preferred as it is easier, faster and less expensive to obtain, and properly generated fragments will already have restriction ends for cloning. For example, Sau3A1 digests of yeast DNA, salmon sperm DNA or calf thymus DNA can be used. Yeast DNA is preferred as it contains little repetitive sequences. However, if the set of markers are to be used in yeast mutant identification, other DNAs should be used.

An example of the preparation of marker fragments from salmon sperm DNA is described below in a–c:

a. Salmon sperm DNA is digested with Sau3A1 to completion. The DNA fragments are fractionated by agarose gel electrophoresis. The gel is cut into 12 slices in the following size ranges:

<100 bp,
100–200,
200–300
300–450
450–600
600–800
800–1k
1–1.2k
1.2–1.5k
1.5–1.8k
1.8–2.2k
2.2–2.6k b. The DNA fragments from each of the gel slices are eluted. The ends are partially filled with dGTP and DATP, cloned into the four insertion plasmid vectors at the SalI site that has been partially filled with dCTP and dTTP, and the ligation mixes are transformed into E. coli. The partial end-filling technique in ligation will ensure that more than 95% of transformants actually contain inserts. A few transformants from each transformation are picked and the sizes of inserts are measured by either restriction digestion or PCR. Two clones with appropriate insert sizes are chosen so that, when they are pooled with other clones sharing the same primers, all of the inserts bands can be clearly resolved on an agarose gel.

c. The results from the above mentioned work are 4 subsets of recombinant plasmids. Each set shares the same pair of primers, and consists of 24 clones with inserts that are different in length. Plasmid DNAs from the 96 clones are prepared and are ready to be introduced into S. aureus.

Alternatively, the insert can be randomly cloned into the vectors to make 4 "insertion libraries". The whole population of each library is used to transform S. aureus RN4220. This is easier and faster, but the information about the input libraries will not be as clear.

Example 2: Introduction of the plasmids into S. aureus chromosome

1). Transformation into S. aureus strain RN4220.

The insert fragments are initially transformed into strain RN4220, which is highly transformable with DNA from E. coli. Therefore, the strain can be used as an intermediate for accepting foreign DNAs and transferring those DNAs to other S. aureus strains. There are at least two methods for introducing the sized markers into the chromosome of RN4220 as described below:

a. Using linearized plasmid DNA. In this method, about 10 µg DNA of each plasmid is linearized with a restriction enzyme that cuts in the vector portion but is highly unlikely to cut in the inserts (e.g., XbaI, ScaI, SgrA1 or AscI). The linearized plasmids are transformed into RN4220 cells by electroporation, for example, in 0.1 cm cuvettes in a Gene Pulser (BIO-RAD) set at 1.5 kv and 100 ohms. Transformants are selected on TS (Trypticase Soy) agar plates containing 1 µg/ml tetracycline. Since the plasmids are linearized, the only tetracycline resistant colonies will come from homologous replacement (double crossover) of the chromosomal sequence with the CIC on the plasmids. The presence of incorporated size markers in the transformants can be detected by PCR using appropriate primers, followed by agarose gel electrophoresis. If somehow the transforming plasmids are not linearized to completion and Tet-resistant colonies arise through integration (i.e.,single crossover recombination), the colonies should also be erythromycin resistant, because the ermC gene would be also introduced. These transformants can be easily distinguished by determining the erythromycin resistance or sensitivity phenotype. An alternative way of checking whether the sized marker fragments are introduced by double crossover or by integration is to use rare cutter restriction enzymes to digest the chromosomal DNA of the transformants. If integration has occurred, an extra site of SmaI, AscI and SgrAI should be present and revealed on pulse field gel electrophoresis (PFGE). On the other hand, only SmaI (present in the CIC), but not the other two rare cutters (present in the vector portion), should be present if double crossover has occurred. This method also shows whether the marker fragments are inserted at the same location or not.

b. Inactivation of the ts-pE194-ori. The circular plasmids containing the sized markers can be transformed into RN4220 by selecting for erythromycin and tetracycline resistance. The transformed cells are then shifted to non-permissive temperature (43° C.) in the presence of tetracycline but not erythromycin. As the plasmids cannot replicate at high temperature, the tet gene is maintained in the cells by either integration (a single crossover event) of the entire plasmid into the chromosome, or gene-replacement (a double-crossover event) between the plasmids and the chromosome. As mentioned above, integration-derived cells are still resistant to erythromycin, but gene-replacement-derived cells become sensitive to this drug. This feature can be easily examined. The two types of cells can also be distinguished by PFGE as described above.

Several rounds of transformation utilizing subsets of clones (24) can be carried out to produce S. aureus RN4220 cells which individually contain each of the 96 marker fragments.

2). Transformation into other strains for actual infection

After the set of strains containing each of the 96 sized markers is constructed in RN4220, the sized markers can be transferred into other strains, e.g., the type strain 8325-4 for mutagenesis and infection into animals. This can be carried out by bacteriophage φ11 mediated transduction. The 96 RN4220 strains carrying the sized markers are individually infected with φ11 at an MOI (multiplicity of infection) of about 0.01 in TS agar plates containing 1 µg/ml tetracycline and 5 mM $CaCl_2$. The lysates are filtered and used to transduce strain 8325-4. Tetracycline resistant transductants are selected on TS agar containing tetracycline and 500 (g/ml sodium citrate. The presence and location of sized markers in the transductants can be similarly detected by PCR and PFGE.

Example 3: Alternate method for the construction and integration of a marker fragment library An alternative method for the construction of a set of S. aureus strains harboring different chromosomally integrated size markers is presented in FIG. 4 and FIG. 5. This system employs genetic components of the staphylococcal phage L54a to provide a mechanism for the site-specific integration of DNA size-markers. Using this system, the markers are stably integrated at the 3' end of the S. aureus geh gene, encoding lipase enzyme (Lee, et al, *Gene* 103:101–105, 1991).

The system uses two plasmid constructions to mediate the integration event. The first plasmid is pMP16/INT; this construction (detailed in FIG. 5) provides functional L54a integrase in trans to S. aureus cells harboring the pMP16/INT plasmid. Transformation of pMP16/INT is by standard protocols available to those skilled in the art; maintenance of the plasmid is by selection on erythromycin supplemented TSA agar (2 ug/ml). The second plasmid is pMP274/CAT/attP. This plasmid has a functional pSC101 replication origin (ori) that supports replication in an E. coli host via selection on media supplemented with spectinomycin. The pSC101 ori is not functional in a S. aureus host, however, thus, transformation of pMP274/CAT/attP plasmid into S. aureus is not compatible with autonomous replication of the plasmid.

Figure 4:
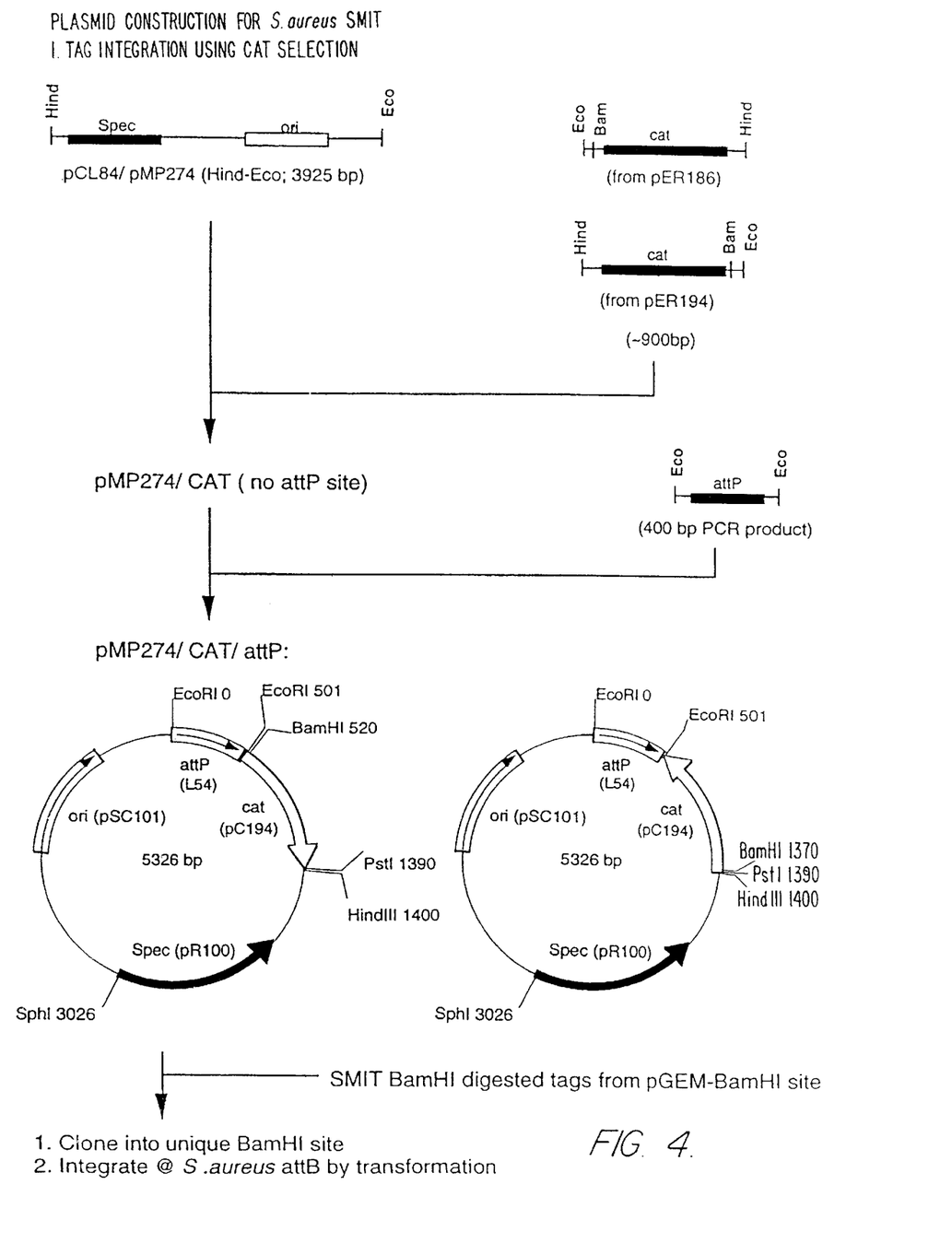
FIG. 4, in conjunction with FIG. 5, summarizes an additional strategy for the construction of marked strains, in this case using genes provided by a bacteriophage of S. aureus, L54a, to mediate stable chromosomal integration of the size markers. The integrase (int) and attachment site (attP) genes from L54a phage are used in this example to provide a means of stably integrating size-markers into the S. aureus chromosomal attB site, located near the 3' end of the lipase structural gene, geh. (Lee, et al, 1991, Gene 103:101–105).
Figure 5:
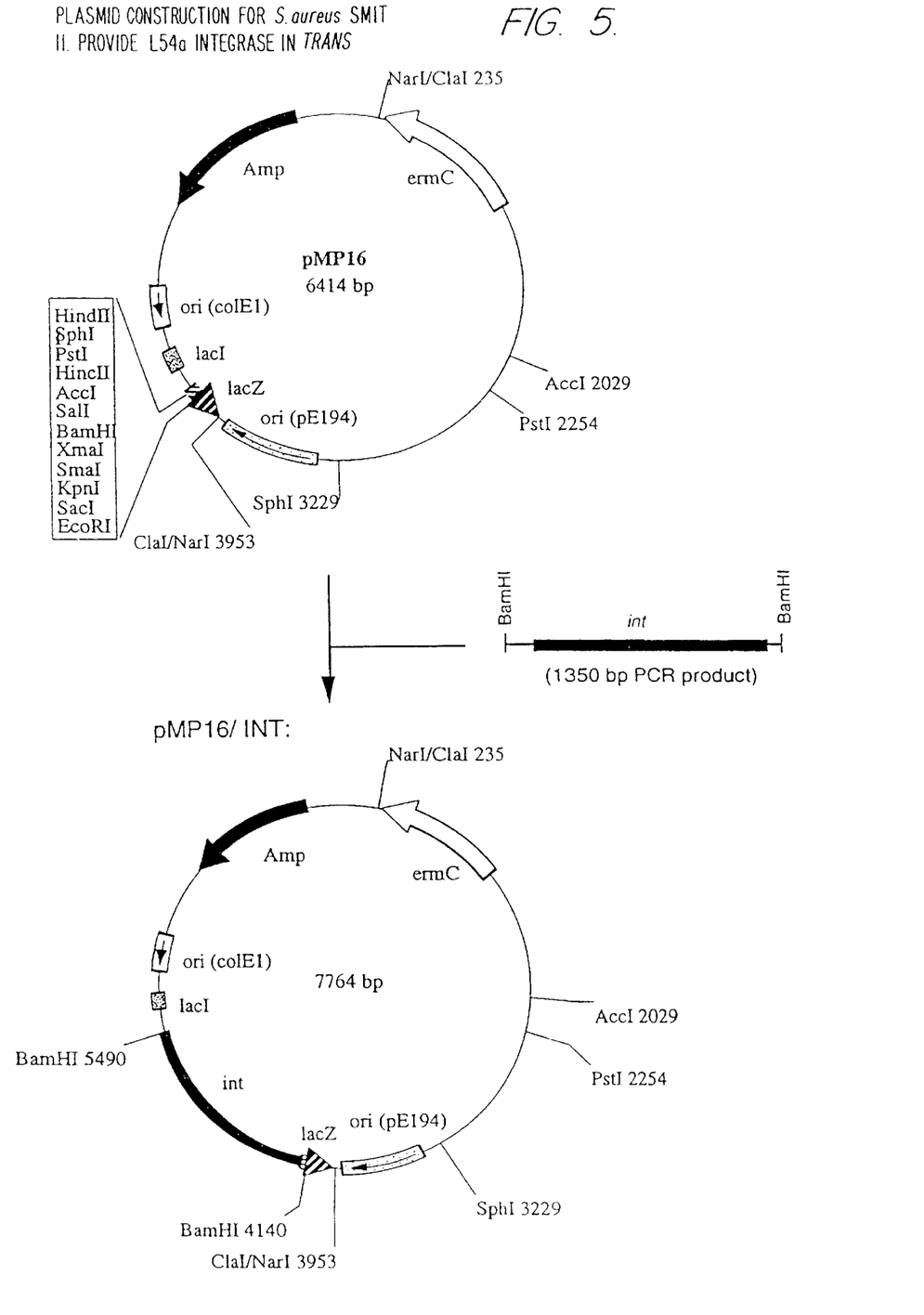

When pMP274/CAT/attP is transformed into a S. aureus host that harbors the pMP16/INT plasmid, integration of the pMP272/CAT/attP plasmid occurs (integrants are selected on TSA agar containing 2–5 ug/ml chloramphenicol). This results from the interaction of integrase (provided in trans by pMP16/INT) and the attP (pMP274/CAT/attP) and chromosomal attB loci. If the incoming pMP274/CAT/attP plasmid carries a size-marker DNA segment in the BamHI site, the marker is integrated along with the plasmid. Thus, different size markers can be stably integrated into the S. aureus genome, providing a marker fragment library for further manipulation, as detailed in Example 4 and Example 5.

Example 4: Mutagenesis and infection

After the whole set of sized markers are introduced into the test strain, mutagenesis can be performed by a variety of means. For example, in transposon Tn917 mutagenesis, the delivery plasmid pLTV1 can be transformed or transduced into each member of the set. Then, each member containing the plasmid is separately mutagenized by temperature shift from 30° C. to 43° C. Many mutants can be isolated from each of these strains, but only one from each culture is pooled. Thus, each pool contains 96 mutants. Approximately equal numbers of cells from each mutant are pooled. An aliquot of each pool is taken as the input sample and used as control.

Each of the pools are then used to infect mice (or other appropriate infection model animal) by an appropriate method. The ideal range of total number of bacterial cells for each infection may be different in different models of in vivo studies, and they can be determined empirically to allow best resolution for mutant identification. After a period of time that is sufficient for infection, in vivo growth and redistribution, but short enough to avoid random population drift, bacteria are recovered from mice (the recovered samples). Chromosomal DNAs are extracted from the recovered samples and subjected to PCR utilizing each of the four sets of primers. The number of PCR cycles can be empirically checked to allow best resolution between different sized markers in the pool and to avoid artifacts that may appear if the number of cycles is too high. The sized marker fragments synthesized by PCR are analyzed by agarose gel electrophoresis. Considering the size range of the fragments (from <100 bp to 2.6 kb), two agarose gels can be used; one is about 2.5–3% agarose for separating bands about <100–700 bp, and the other one about 0.7% agarose for separating bands between 500 bp and 2.5 kb. DNA extracted from the input samples as well as from the same cells after certain period of in vitro growth in rich medium can be used as controls. A DNA fragment that is present in the control PCR samples but absent or under represented in the recovered samples indicates that the mutant carrying that fragment may be unable to survive or grow in vivo. The mutant can be easily identified by the size of its characteristic marker band. The gene(s) affected in that mutant can be isolated.

Example 5: Application of SMIT-PCR technology using a mixed population of tagged cells containing a defined attenuated mutant of S. aureus and an isogenic wild type S. aureus A specific application of SMIT-PCR technology using differentially marked strains of avirulent S. aureus (ndk/aroC) and isogenic wild type S. aureus is described. In this example, the rat peritoneal implant chamber model (Pike, et al, *Microbial Pathogen.* 10:443–450, 1991) was used as the in vivo setting for evaluating input and output pools of the marked strains. This model contains the input organisms in a diffusion chamber that has two 0.22 um membrane filters on either end to allow for passage of in vivo nutrients to the organisms. Since the organisms do not escape from the chamber, but are nonetheless exposed to the in vivo environment while present in the peritoneal cavity, they expand only in the chamber. Thus, comparison of input and output organisms is simplified for the practice of SMIT-PCR.

The strains comprising the input pool were SAM884, a wild type *S. aureus*, and SAM962 and SAM961, two versions of the avirulent *S. aureus* ndk/aroC mutant. Each of the three strains carried a distinct DNA size marker in the geh locus, integrated into the respective chromosomes using the strategy outlined in Example 3 and detailed in FIGS. 4 and 5.

Figure 6:
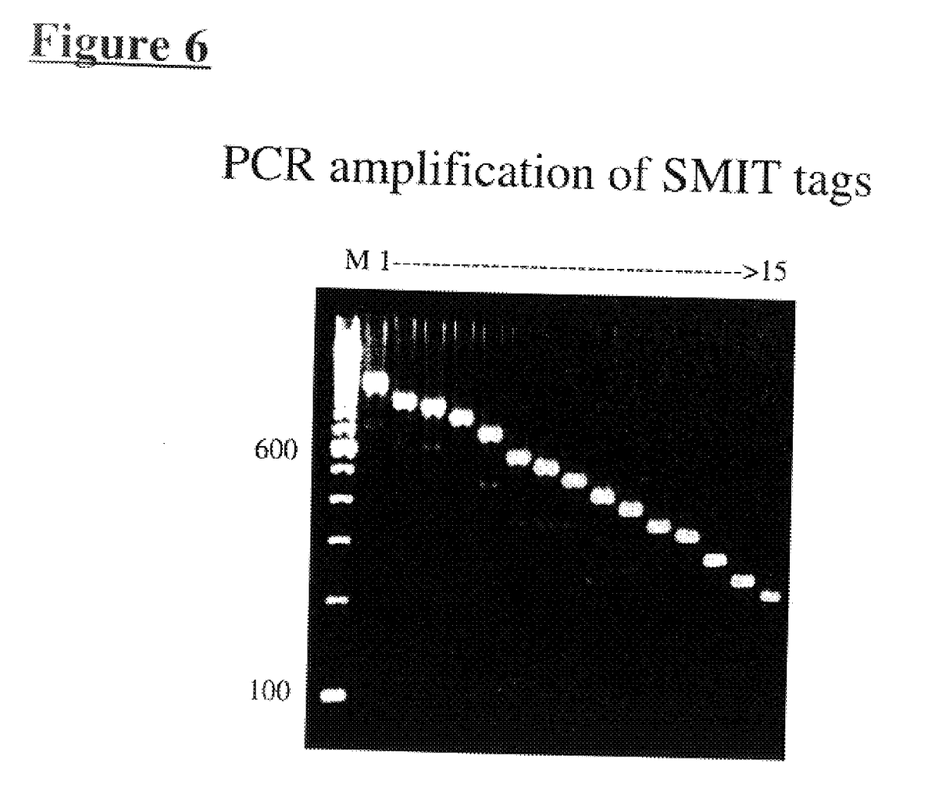
FIG. 6 illustrates the range of size-markers used to individually mark cells of S. aureus; fifteen independently isolated size-markers are depicted. Tags were derived from salmon sperm DNA by Sau3AI digestion, size fractionation on agarose gels, and cloning into the BamHI site of pGEM3Zf(+) with white colony selection. Lanes: M, 100 bp ladder; 1–15, SMIT tag amplification products derived from fifteen independently isolated pGEM::tag clones.

The markers were derived from the fifteen member tag set depicted in FIG. 6 and corresponded to random Sau3A fragments of salmon sperm DNA.

In this example, the input inoculum placed in the peritoneal chamber consisted of roughly equal titers of the three organisms ($10^3$ cfu/ml); samples of this initial mixed inoculum were plated and DNA prepared from the collective cells. PCR amplification using this pooled DNA and "universal" primers capable of amplifying all three tags, provided the DNA products shown in FIG. 7 (lane: input pool).

Figure 7:
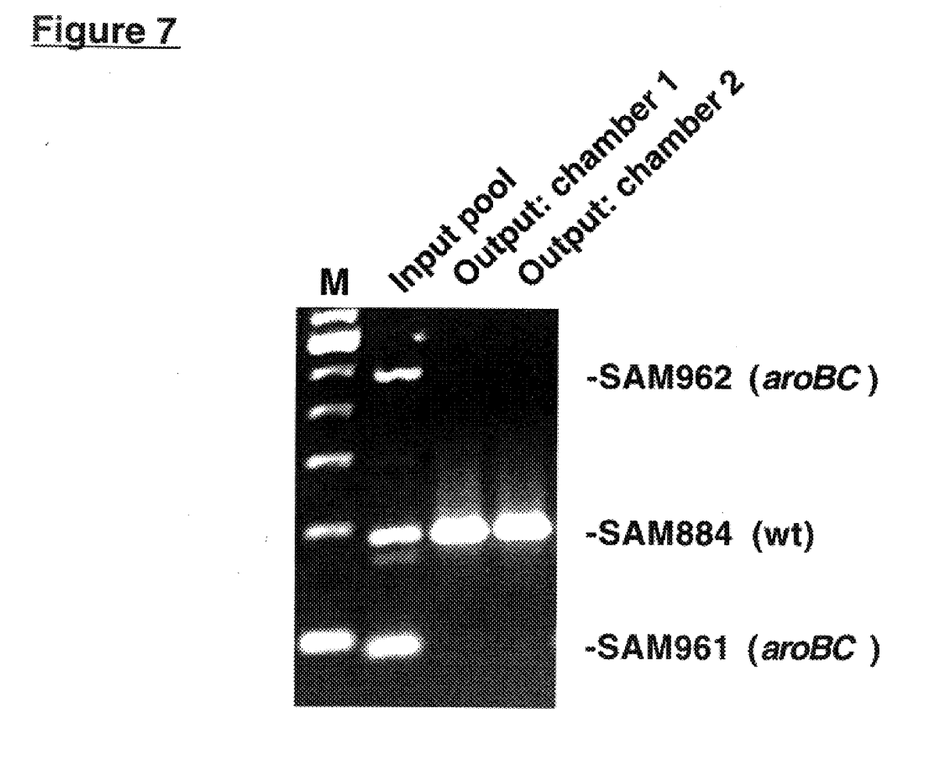
FIG. 7 shows the results of a SMIT-PCR experiment employing two differentially tagged versions of a confirmed avirulent S. aureus mutant (ndk/aroC), SAM962 and SAM961, and a tagged wild type S. aureus, SAM884. Experimental details are given in Example 4. Lanes: M, 100 bp ladder; input pool, PCR products obtained using DNA extracted from a 1:1:1 mix of SAM962, SAM961, and SAM884 (final titer $10^3$ cfu/ml) used to inoculate a peritoneal chamber implanted in a rat; output: chamber 1 and output: chamber 2, PCR products obtained using DNA extracted from SAM962, SAM961, and SAM884 cells recovered from implanted peritoneal chambers at 24 hrs post-placement, in two different rats. The output chamber results in FIG. 7 clearly demonstrate the principal behind SMIT-PCR, in that size-marker signals corresponding to the avirulent mutants SAM962 and SAM961 were not detected in the collection of recovered cells, whereas the signal for the wild type organism (SAM884) was readily detected.

The pooled inoculum containing SAM884, SAM962, and SAM961 was incorporated into two separate chambers and placed into the peritoneal cavities of two separate rats. After 24 hrs post-placement of the chambers, the rats were sacrificed and the chambers recovered. Appropriate dilutions of the "output" chamber contents were plated on TSA agar plates; colonies were collected from an "output" plate containing roughly 1000 colonies, for each chamber. DNA was prepared from the pooled "output" colonies and subjected to PCR, as described for the input inoculum. The products of the output DNA PCR reaction are shown in FIG. 7 (lanes: output, chamber 1 and output, chamber 2). DNA size-marker signals corresponding to the two avirulent ndk/aroC mutants (SAM962 and SAM961) are absent from the recovery, output pool, suggesting that these cells do not survive exposure to the in vivo environment. The signal corresponding to the wild type SAM884 cells is represented in the recovery pool, indicating growth of these cells in the in vivo environment.

Example 6: Cloning of a gene involved in growth

If a mutant is found to be defective for in vivo growth and pathogenesis, the gene affected can be cloned by various methods. If the mutagen is the above-mentioned Tn917 that contains the amp gene for ampicillin resistance and a replication origin functional in *E. coli*, a portion of the gene interrupted by the transposon in that mutant can be obtained by digesting the chromosomal DNA with appropriate restriction enzymes, and transforming the self-ligated fragments into *E. coli*. Upon isolating ampicillin resistant colonies, plasmids that carry a portion of the gene are obtained. DNA sequencing analysis of the gene portion will reveal whether it is a known gene, or a gene that is unknown in *S. aureus* but its homologues are known in other bacteria, or a totally unknown gene. To obtain a full copy of the gene, the available portion can be used as probe to screen a plasmid or phage library or sublibrary. Sometimes further chromosomal walking procedures may be required to completely isolate the whole gene and/or the whole operon.

Another method of cloning the mutant gene is to find in vitro phenotypes associated with the gene. Such phenotypes allow recognition of complementary clones by restoration of the wild type phenotype to the mutant strain.

An alternative way of cloning the mutant gene is by plasmid complementation, in which a plasmid carrying the wild type form of the gene is identified by its ability to restore the in vivo growth of the mutant. In this case, a genomic library is transduced into the mutant that failed to grow (or grew poorly) in vivo. Colonies of transductants are pooled and used to infect mice. After an appropriate period of time bacteria are recovered. Those that have survived the in vivo environment and have increased in numbers may contain the corresponding wild type gene in the plasmid. Sometimes, a few rounds of in vivo enrichment of these bacteria cells are needed to single out the true complementing clones.

Example 7: Other mutagenesis methods

The parental set can also be mutagenized by other means like chemical mutagenesis, UV treatment and in vitro mutagenesis. For example, diethyl sulfate (DES) can be used as a chemical mutagen in SMIT. In this case, members of the parental set of *S. aureus* strains are individually grown in TS broth in a 96-well microtiter plate. After overnight growth, 2 $\mu$l of each culture is transferred into another 96-well plate containing 100 $\mu$l $\lambda$ dilution buffer in each well. To each well 1–2 $\mu$l of DES is added. The actual amount of DES added can be empirically determined to achieve maximum mutagenesis efficiency while avoiding too much killing and/or a high rate of multiple mutations. In general, a survival rate around 0.1–0.2% is a good compromise and can be used as a start point in determining the optimal conditions. The plate is incubated at 35° C. for 20 min. The mutagenized minicultures are then properly diluted in into fresh TS broth in a number of 96-well plates and incubated at 35° C. for 6–12 hr. The dilutions are plated on TS agar plates. One colony from each well is picked and pooled with a colony from other minicultures. As not all of the colonies carry mutations, more pools than with the Tn917 mutagenesis may be required to assure the inclusion of mutations in most of genes. Alternatively, colonies with certain phenotypes such as changes in colonial morphology and cellular shapes are picked and pooled. The pools are used to infect mice. Mutants that fail to survive and grow in vivo can be identified as described above.

Members of the parental set can also be individually treated with ultraviolet light (UV) to generate mutants. Cells grown in 100 $\mu$l of TS broth in 96-well plates at OD600=1.0 are pelleted by centrifugation and resuspended in equal volume of 0.15 mM NaCl and 4 mM $CaC_2$. The cells are diluted 10-fold in the same solution and aliquoted in new microtiter plates. The final volume in each well is significant, as this affects mutagenesis efficiency. To start with, 50–100 $\mu$l can be used. The plate is irradiated with a UV generating lamp at about 254 nm. The distance between the UV lamp and the plate, and the duration of irradiation can be determined empirically to reach maximum mutation frequency while avoiding too much killing and multiple mutation. If a standard hand-held UV lamp is used, a distance of 20 cm and 30–35 seconds of irradiation will result in about 0.2–0.05% survival rate, which can be used as a starting point to search for optimal conditions. The plate is shaken gently during UV irradiation. To each of the UV-treated minicultures, equal volume of 2×TS broth is added and the plate is incubated at 35° C. for 6–12 hr. The cultures are properly diluted and plated on TS agar plates. Colonies of each culture are pooled and used to infect mice as described above.

In vitro mutagenesis methods are not suitable for generating mutants for identifying bacterial in vivo essential genes. However, it can be combined with the SMIT for many other purposes. Using SMIT and in vitro mutagenesis, one can identify specific mutations that confer certain phenotypes. There are many diverse methods of in vitro mutagenesis. The gene or genes (or viral genomes) can be mutagenized in vitro by an appropriate method—those who work in the field will know which in vitro method should be used for particular applications. The population of mutagenized DNA molecules are then reinserted in cells of the marked parental set, such as bacteria, fungi, animal cell lines, etc. One clone containing a mutation from each member of the parental set is pooled and the pools are subjected to test conditions. Mutations that are unfavored (or favored) under the test conditions can be tracked and identified by examining the absence/presence and the intensity of specific sized markers through PCR and agarose gels.

Example 8: Use of SMIT in other systems

The SMIT technology can be applied to a broad range of organisms including various Gram positive and Gram negative bacteria, viruses, fungi, insects, plant and animal cell lines. A brief description is provided below.

a. Other bacteria. With only minor modifications, the SMIT can be applied to other bacteria. The sized markers can be similarly introduced into bacterial cells by homologous recombination or by prophages as a vehicle to construct a parental set. Similar mutagenesis methods can be used for various bacteria. In addition to identifying in vivo essential genes, genes involved in in vitro growth under certain stress conditions can be identified. These include genes involved in stationary phase survival, in survival and growth under various culture conditions (low irons, high salt, low or high pH, etc.), in survival and growth under the extreme conditions of their natural habitat (e.g., extreme high temperature for thermophiles, extreme high salt for halophiles, etc.), in the ability to metabolize certain rare substrates (e.g., genes involved in decomposing organic materials and oil), in their persistence in certain ecosystems, and in their ability to transmit from one host to others. Besides identification of genes, the differentially marked cells can be used to monitor the distribution and spread of the cells in their natural habitat, which will help to understand and control the transmission of the bacteria. The above list of usages of SMIT in bacteria is only exemplary. Numerous other applications in which the identification of particular bacterial strains is useful will be apparent to those skilled in the art.

b. Viruses. SMIT can be applied as well to viral studies. A set of parental viral strains can be similarly marked by sized DNA fragment. As viral genomes are small, the capacity of accepting extra DNA is often limited. Therefore, smaller sized markers may preferably be used. Addition of sized markers is accomplished through homologous recombination, or, for viruses with small genomes, recombinant techniques can be used. To increase the resolution of sized markers after PCR, polyacrylamide gel separation may be required. After the parental set is constructed, the whole virus or viral DNA can be mutagenized by appropriate means either within or outside host cells. Alternatively, a portion of viral DNA to be studied can be cloned and mutagenized by in vitro mutagenesis and then recombined to the parental set. One viral plaque from each member of the set is picked, pooled, and subjected to the test conditions. After an appropriate time (determined by the particular virus/cell system), the viruses are recovered and the sized markers are analyzed to determine the fate of particular mutants. Mutants that fail to survive and grow can then be identified. This method identifies not only genes essential under the test conditions, but also specific nucleotides that are vital for the function of these genes. The latter issue is often more important, as functions of the few genes in a virus may already be known, and studies are focusing on what part of the gene is critical to its function. For example, to study the binding of a virus to its receptor on a host cell, it is important to know what sites of the viral envelope protein(s) are critical for such binding. Combining SMIT and appropriate mutagenesis methods and binding assays, these sites can be readily identified. Information such as this can be used to develop methods to control the virus (such as developing antibodies toward the specific sites, develop ligands to the sites to block the binding, etc.).

c. Fungi. Construction of a parental set of size-marked strains in fungi can be done by available genetic methods. For example, in the yeast, *Saccharomyces cerevisiae*, the sized-markers on a delivery plasmid can be introduced into cells by transformation and homologous recombination. Most classic mutagenesis methods can be performed in fungi. One mutant from each member of the parental set is picked, pooled, and subjected to test conditions. Various types of fungal genes can be identified using the SMIT, including those involved in fungal pathogenesis and in vivo growth, in response to environmental stresses, in decomposing certain waste or polluting materials, etc. Since fungi have multiple chromosomes, it is important to prevent exchange of genetic materials (such as mating and meiosis) between individuals as this will likely recombine the chromosome carrying the sized markers and that carrying the mutations.

d. Insects. The parental set of strains can be constructed through site-directed gene delivery systems available in the species of interest. Germ lines should be targeted to make the sized markers stably inherited. Researchers working in the field of a particular insect species should be familiar with the appropriate methods of such construction. Once constructed, the size-markers in each member of the set can be maintained by inbreeding the homozygous insects, or by monitoring the segregation of the markers by PCR. As the sized markers can be viewed as a set of alleles, they can be used to study genetic recombination and gene frequency shift. The markers can also be used to study migration and spread of agriculturally or medically important insect pests. Such information will help to develop methods of preventing the transmission and spread of the pests and eventually control them.

e. Plant and animal cell lines. Cultured cells can be viewed as microorganisms in that a large population can be cultured and that little genetic exchange occurs between "generations". SMIT can be applied to cultured cells to address questions including but not limited to: What genes are involved in binding of the cells to certain ligands? What genes are responsible for hypersensitivity to challenges such as viruses or bacterial invasion, prolonged incubations, shift in temperature, pH, osmolarity, etc.? Where and how cultured cells travel, propagate and differentiate when they are sent back to the animal host? What genes are involved in the in vivo transport, propagation, and differentiation of the cells?

To construct a set of parental cell lines, different sized marker are first constructed in a vector system (a viral or plasmid vector). The DNAs carrying the sized markers are introduced into cultured animal cells by transfection, electroporation, or viral-mediated procedures. Plant cells can be marked by transfection with specific plasmid DNA (such as Ti plasmids) carrying the sized markers, by electroporation, or by bombardment with micro projectiles coated with the DNA. Researchers familiar with the fields will know what procedures and vectors to use for constructing the recombinant DNA carrying the markers and for transfection and selection for particular cells. Like microorganisms, the cultured cells can be mutagenized by various means, including chemical mutagens, UV, site-directed mutagenesis and so on. One mutant from each member of the set is picked, pooled, and subjected to test conditions. For example, if the purpose is to find mutants that are hypersensitive to certain stress condition, equal numbers of cells from each mutant will be pooled and grown under that condition. After incubation for a given period of time, cells are recovered and mutants that fail to survive or grow are identified by similar procedures as described above. If the purpose is to study the redistribution and fate of cells in the host, marked cells or a pool of mutated marked cells can be injected back to an suitable host animal. The distribution and differentiation of these cells are then examined. This type of study will provide information on the route of transport and differentiation of certain cells (such as lymph cells and blood cells) and what genes are critical these processes inside the animal body.

The embodiments and methods described herein are not meant to be limiting to the invention. Those skilled in the art will recognize that the methods for constructing a set of strains for SMIT can be performed in many different ways besides those described above and in a large variety of different organisms. They will further recognize that SMIT can be used in a large variety of different applications in addition to those described. Thus, such additional methods and applications are all within the breadth of the claims.

Other embodiments are within the following claims.

We claim:

1. A method for identifying a strain of cells containing a mutation in a gene involved in growth, comprising the steps of:
    a) forming a labeled set of strains comprising a plurality of members, each member of said set containing an exogenous DNA fragment of a defined length stably integrated into the chromosome of said member, said defined length in each said member differing from said defined length in other said members,
    b) subjecting said labeled set of strains to mutagenesis so as to obtain mutants from each member of said set of strains, and
    c) introducing cells of said mutant strains into a growth environment for a period of time sufficient for growth of a non-mutated strain and determining which strains have altered growth compared to a non-mutated strain, by determining the presence and size of said exogenous DNA fragments relative to each other.

2. The method of claim 1 wherein said strains of cells are selected from the group consisting of bacteria, fungi, plant cells, and animal cells.

3. The method of claim 1, wherein said mutagenesis comprises the use of a transposon or other insertional mutagen.

4. The method of claim 1, wherein said mutagenesis comprises chemical mutagenesis.

5. The method of claim 1, wherein said mutagenesis occurs spontaneously.

6. The method of claim 1, wherein said mutagenesis comprises the use of a physical mutagen.

7. The method of claim 6, wherein said physical mutagen comprises ultraviolet light.

8. The method of claim 1, wherein said mutagenesis comprises the use of in vitro mutagenesis using recombinant DNA techniques.

9. The method of claim 1, wherein the presence and size of said exogenous DNA fragments is determined by PCR followed by gel electrophoresis.

10. The method of claim 1, further comprising the step of identification of said gene involved in growth contained in said mutant strain having reduced growth compared to a non-mutated strain in said growth environment.

11. The method of claim 2 wherein said bacteria is of the species *Staphylococcus aureus*.

12. The method of claims 1, wherein said growth environment comprises an animal host.

13. The method of claim 1, wherein integration of said exogenous DNA fragment is at the same chromosomal location in all members of said plurality of members.

14. A method for producing a plurality of labeled cells which can be individually identified, comprising the step of:
    introducing into a plurality of separate cells an exogenous DNA fragment which differs in length in each said separate cell, and which stably insert into a chromosome of each said separate cell.

15. The method of claim 14 wherein said cells are selected from the group consisting of bacteria, fungal cells, plant cells, and animal cells.

16. The method of claim 15, wherein said cells are bacteria of the species *Staphylococcus aureus*.

17. The method of claim 14, wherein integration of said exogenous DNA fragment is at the same chromosomal location in all members of said plurality of labeled cells.

18. A set of labeled cells wherein a chromosome of each cell of said set contains an exogenous DNA fragment which differs in length between each member of said set.

19. The set of claim 18, wherein said cells are selected from the group consisting of bacteria, fungal cells, plant cell, and animal cells.

20. The set of claims 19, wherein said bacteria are of the species *Staphylococcus aureus*.

21. A method for monitoring the distribution or fate of a cell in a growth environment comprising the steps of:
    forming a labeled cell with an exogenous DNA fragment of a defined length stably integrated into the chromosome of said cell,
    introducing said labeled cell into said growth environment for a period of time sufficient for growth of said cell and determining the distribution or fate of said cell by the presence of said exogenous DNA fragment.

22. The method of claim 21, wherein said determining the distribution or fate of said cell by the presence of said exogenous DNA fragment is performed by PCR followed by gel electrophoresis.

23. A method for identifying a strain of viruses containing a mutation in a gene involved in growth in a cell, comprising the steps of:
    a) forming a labeled set of strains comprising a plurality of members, each member of said set containing an exogenous DNA fragment of a defined length stably integrated into the chromosome of said member, said defined length in each said member differing from said defined length in other said members,
    b) subjecting said labeled set of strains to mutagenesis so as to obtain mutants from each member of said set of strains, and c) introducing viruses of said mutant strains into a growth environment for a period of time sufficient for growth of a non-mutated strain and determining which strains have altered growth compared to a non-mutated strain, by determining the presence and size of said exogenous DNA fragments relative to each other.

24. The method of claim 23, wherein said mutagenesis comprises chemical mutagenesis.

25. The method of claim 23, wherein said mutagenesis occurs spontaneously.

26. The method of claim 23, wherein said mutagenesis comprises the use of a physical mutagen.

27. The method of claim 26, wherein said physical mutagen comprises ultraviolet light.

28. The method of claim 23, wherein said mutagenesis comprises the use of in vitro mutagenesis using recombinant DNA techniques.

29. The method of claim 23, wherein the presence and size of said exogenous DNA fragments is determined by PCR followed by gel electrophoresis.

30. The method of claim 23, further comprising the step of identification of said gene involved in growth contained in said mutant strain having reduced growth compared to a non-mutated strain in said growth environment.

31. The method of claim 23, wherein said growth environment comprises an animal host.

32. A method for producing a plurality of labeled viruses which can be individually identified, comprising the step of:
   introducing into a plurality of separate viruses an exogenous DNA fragment which differs in length in each said separate virus, and is able to stably insert into a chromosome of each said separate virus.

33. The method of claim 32, wherein integration of said exogenous DNA fragment is at the same chromosomal location in all members of said plurality of members.

34. A set of labeled viruses wherein a chromosome of each virus of said set contains an exogenous DNA fragment which differs in length between each member of said set.

* * * * *